US012347559B2

(12) United States Patent
Sharma et al.

(10) Patent No.: US 12,347,559 B2
(45) Date of Patent: Jul. 1, 2025

(54) GENOMIC BIOMARKER PREDICTION FROM MEDICAL IMAGES

(71) Applicant: Rakuten Group, Inc., Tokyo (JP)

(72) Inventors: Shreya Sharma, Karnataka (IN);
Srikanth Ragothaman, Karnataka (IN);
Shantanu Majumdar, Karnataka (IN)

(73) Assignee: Rakuten Group, Inc., Tokyo (JP)

( * ) Notice: Subject to any disclaimer, the term of this patent is extended or adjusted under 35 U.S.C. 154(b) by 427 days.

(21) Appl. No.: 17/876,713

(22) Filed: Jul. 29, 2022

(65) Prior Publication Data

US 2024/0038388 A1     Feb. 1, 2024

(51) Int. Cl.
*G16H 50/20* (2018.01)
*G06T 7/00* (2017.01)
*G06V 10/22* (2022.01)
*G06V 10/40* (2022.01)
*G06V 10/764* (2022.01)
*G06V 10/82* (2022.01)
*G16H 30/40* (2018.01)
*G16H 50/30* (2018.01)

(52) U.S. Cl.
CPC .......... *G16H 50/20* (2018.01); *G06T 7/0014* (2013.01); *G06V 10/22* (2022.01); *G06V 10/40* (2022.01); *G06V 10/764* (2022.01); *G06V 10/82* (2022.01); *G16H 30/40* (2018.01); *G16H 50/30* (2018.01); *G06T 2207/20081* (2013.01); *G06T 2207/20084* (2013.01); *G06T 2207/30096* (2013.01); *G06V 2201/032* (2022.01)

(58) Field of Classification Search
None
See application file for complete search history.

(56) References Cited

U.S. PATENT DOCUMENTS

2022/0130547 A1*   4/2022   Grady .................... G16H 30/40
2023/0153994 A1*   5/2023   Liu ......................... G06T 7/136
                                                                  382/128

OTHER PUBLICATIONS

Apaar Sadhwani et al., "Comparative analysis of machine learning approaches to classify tumor mutation burden in lung adenocarcinoma using histopathology images", Scientific Reports, 2021, vol. 11, No. 16605, pp. 1-11 (11 pages total).

* cited by examiner

*Primary Examiner* — Mark R Milia
(74) *Attorney, Agent, or Firm* — Sughrue Mion, PLLC

(57) ABSTRACT

A method, apparatus, and non-transitory computer-readable medium are provided for image processing of medical images. The method may include receiving one or more medical images. Tissue regions may be identified in each of the one or more medical images. The method may include generating patches associated with respective identified tissue regions. A patch tumor burden (TMB) score may be predicted for each of the patches based on a neural network model, wherein the neural network model is trained using a distribution smoother and a weighted loss function. The method may also include a tumor burden score being generated for each of the one or more medical images based on the patch tumor burden score for patches associated with the respective identified tissue regions in respective medical images from the one or more medical images.

20 Claims, 4 Drawing Sheets

GENOMIC BIOMARKER PREDICTION FROM MEDICAL IMAGES

FIELD

The present disclosure relates to image processing. More particularly, the present disclosure relates to image processing using machine learning.

BACKGROUND

Genetic markers or genomic biomarkers are increasingly used while prescribing cancer immunotherapies. As an example, Tumor Mutational Burden (TMB) is a leading genomic biomarker used in cancer immunotherapy. Higher or lower values associated with genomic biomarkers are associated with better immunotherapy responses for certain cancers and for separating responding and non-responding patients. For example, high TMB values are associated with better immunotherapy response in lung cancer as well as other solid tumors. In addition, TMB has shown predictive power for separating responding and non-responding patients in many clinical trials. Oncologists are therefore increasingly considering genomic biomarkers in their decision to prescribe immunotherapy. However, traditional methods to measure genomic biomarkers based on whole-exome sequencing (WES) and genomic data processing is highly time-consuming, resource-consuming, and costly which restrict its availability to many patients.

Therefore, methods of determining genomic biomarker values that leverage widely available resources and more accessible technologies are needed.

SUMMARY

Embodiments relate to a method, system, and computer readable medium for image processing of medical images to predict a genomic biomarker score.

According to one aspect, a neural network based method for image processing of medical images is provided. The method may be executed by one or more processors and may include receiving one or more medical images; identifying tissue regions in each of the one or more medical images; generating patches associated with respective identified tissue regions; predicting a patch tumor burden score for each of the patches based on a neural network model, wherein the neural network model is trained using a distribution smoother and a weighted loss function; and generating a tumor burden score for each of the one or more medical images based on the patch tumor burden score for patches associated with the respective identified tissue regions in respective medical images from the one or more medical images.

According to another aspect, an apparatus for a neural network based framework for image processing of medical images may be provided. The apparatus may include a memory storing instructions; and at least one processor configured to execute the instructions. The instructions may include receive one or more medical images; identify tissue regions in each of the one or more medical images; generate patches associated with respective identified tissue regions; predict a patch tumor burden score for each of the patches based on a neural network model, wherein the neural network model is trained using a distribution smoother and a weighted loss function; and generate a tumor burden score for each of the one or more medical images based on the patch tumor burden score for patches associated with the respective identified tissue regions in respective medical images from the one or more medical images.

According to yet another aspect, a non-transitory computer-readable medium storing instructions for a neural network based method for image processing of medical images, may be provided. The instructions may include one or more instructions that, when executed by one or more processors, cause the one or more processors to receive one or more medical images; identify tissue regions in each of the one or more medical images; generate patches associated with respective identified tissue regions; predict a patch tumor burden score for each of the patches based on a neural network model, wherein the neural network model is trained using a distribution smoother and a weighted loss function; and generate a tumor burden score for each of the one or more medical images based on the patch tumor burden score for patches associated with the respective identified tissue regions in respective medical images from the one or more medical images.

BRIEF DESCRIPTION OF THE DRAWINGS

These and other objects, features and advantages will become apparent from the following detailed description of illustrative embodiments, which is to be read in connection with the accompanying drawings. The various features of the drawings are not to scale as the illustrations are for clarity in facilitating the understanding of one skilled in the art in conjunction with the detailed description. In the drawings.

DETAILED DESCRIPTION

Figure 1:
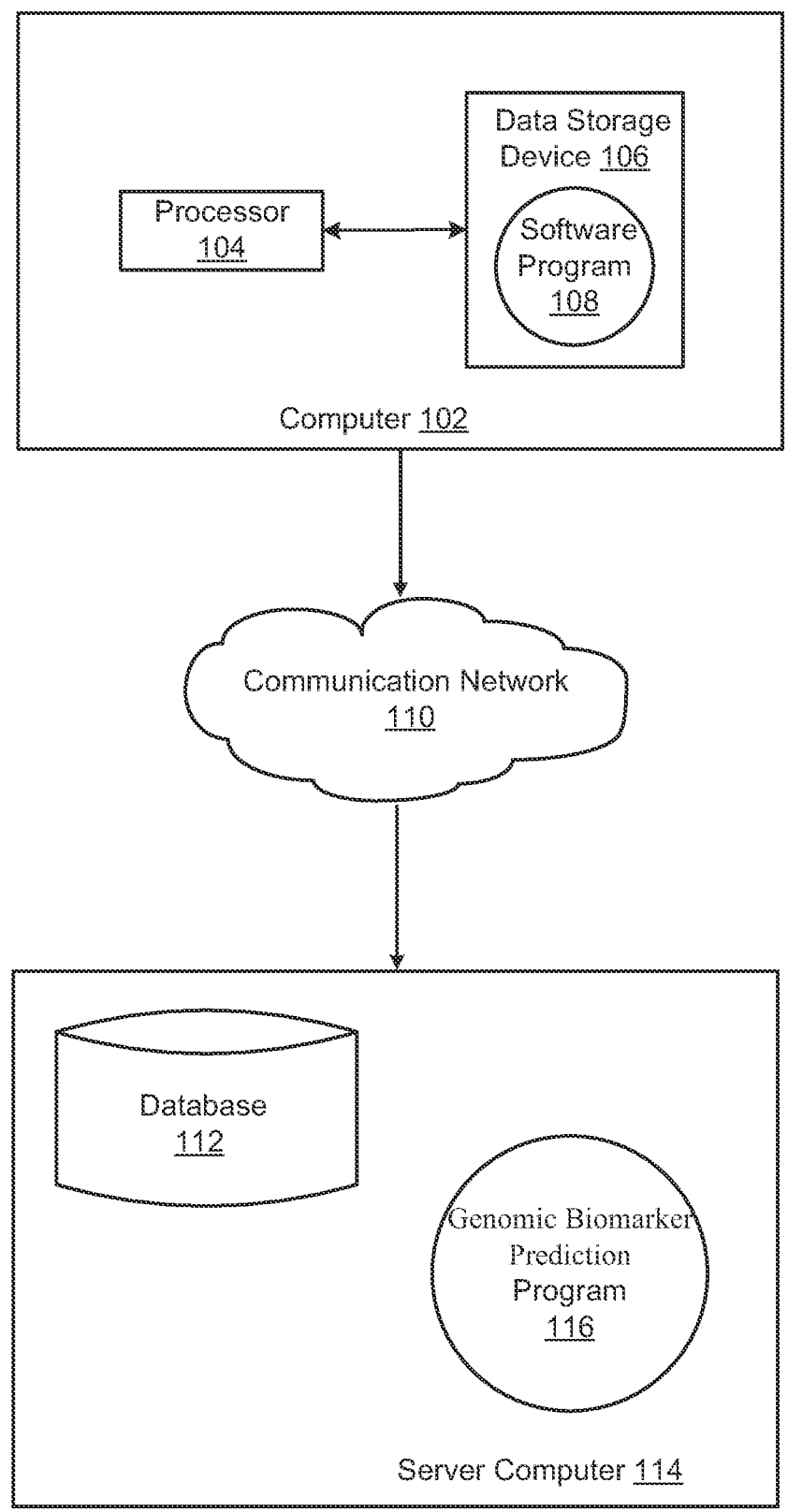
FIG. 1 illustrates a networked computer environment according to an embodiment.

Detailed embodiments of the claimed structures and methods are disclosed herein; however, it can be understood that the disclosed embodiments are merely illustrative of the claimed structures and methods that may be embodied in various forms. Those structures and methods may, however, be embodied in many different forms and should not be construed as limited to the exemplary embodiments set forth herein. Rather, these exemplary embodiments are provided so that this disclosure will be thorough and complete and will fully convey the scope to those skilled in the art. In the description, details of well-known features and techniques may be omitted to avoid unnecessarily obscuring the presented embodiments.

Embodiments of the present disclosure are generally relating to image processing, and more particularly to machine learning. The following described exemplary embodiments provide a system, method and computer program to, among other things, segment image data and extract features from image data. Therefore, some embodiments have the capacity to improve the field of computing by allowing for the use of selectively locating and determining a tumor mutational burden (TMB) values in medical images such as histopathology images. According to embodiments, throughout the present specification, histopathology images are used as a non-limiting example of medical image that may be used. Any suitable medical images may be used.

In related art, processing histopathology images is exclusively a classification task to predict whether a tumor is TMB-high or TMB-low. Such classification has low utility as it provides limited flexibility to pathologists to select appropriate thresholds themselves and stratify patients into more than two categories. However, since there are no standard threshold TMB values as they vary across cancer types, a mere classification of TMB-high or TMB-low is a significant drawback of related art. Furthermore, related art methods applied for regression tasks to predict continuous TMB scores consistently have low performance due to huge data imbalance in the target values, where certain TMB scores have significantly fewer observations. As an example, models may be biased towards low values of markers due to imbalanced distribution which leads to low accuracy.

Therefore, systems, methods, and computer programs are provided herein that process readily available histopathology images and directly predict genomic markers using deep learning regression models. According to an aspect of the disclosure, a distribution smoother may be employed during model training to estimate an expected distribution of training labels based on continuity of labels to compensate for the data imbalance. The estimated distribution may be used to derive weights of samples and train the model with a weighted loss function. As a result, the model may effectively from both majority and minority frequency samples and generalize over the entire TMB score range.

According to embodiments of the disclosure, predicting continuous TMB scores instead of discrete classes has more practical application in clinics and provides flexibility to pathologists to select appropriate thresholds themselves. Furthermore, the models disclosed herein may be generalized over the continuous TMB score range in an imbalanced setting based on using a distribution smoother and a weighted loss function. The generalized genomic biomarker prediction framework disclosed herein may be expanded to other cancer types and biomarkers such as Microsatellite Instability Biomarker (MSI)/deficiency Mismatch Repair (dMMR), Chromosomal Instability Biomarker (CIN). Predicting genomic biomarkers directly from medical image will save cost of genomic testing, improve therapy outcomes, and enrich genomic datasets.

The following described exemplary embodiments provide a generalized process to predict continuous TMB score ranges in an imbalanced setting by using a distribution smoother and a weighted loss function. While exemplary embodiments herein are described with reference to predict continuous TMB score ranges from histopathology images, it is understood that the present disclosure is not limited thereto and may be applicable to any genomic biomarker prediction for other cancer types and biomarkers therein.

Referring now to FIG. 1, a functional block diagram of a networked computer environment illustrating an image processing system 100 (hereinafter "system") for TMB score prediction from histopathology images. It should be appreciated that FIG. 1 provides only an illustration of one implementation and does not imply any limitations with regard to the environments in which different embodiments may be implemented. Many modifications to the depicted environments may be made based on design and implementation requirements.

The system 100 may include a computer 102 and a server computer 114. The computer 102 may communicate with the server computer 114 via a communication network 110 (hereinafter "network"). The computer 102 may include a processor 104 and a software program 108 that is stored on a data storage device 106 and is enabled to interface with a user and communicate with the server computer 114. As will be discussed below with reference to FIG. 4 the computer 102 may include internal components 800A and external components 900A, respectively, and the server computer 114 may include internal components 800B and external components 900B, respectively. The computer 102 may be, for example, a mobile device, a telephone, a personal digital assistant, a netbook, a laptop computer, a tablet computer, a desktop computer, or any type of computing devices capable of running a program, accessing a network, and accessing a database.

The server computer 114, which may be used for genomic biomarker prediction, is enabled to run a Genomic Biomarker Prediction Program 116 (hereinafter "program") that may interact with a database 112. Genomic Biomarker Prediction Program method is explained in more detail herein. In one embodiment, the computer 102 may operate as an input device including a user interface while the program 116 may run primarily on server computer 114. In an alternative embodiment, the program 116 may run primarily on one or more computers 102 while the server computer 114 may be used for processing and storage of data used by the program 116. It should be noted that the program 116 may be a standalone program or may be integrated into a genomic biomarker prediction program.

It should be noted, however, that processing for the program 116 may, in some instances be shared amongst the computers 102 and the server computers 114 in any ratio. In another embodiment, the program 116 may operate on more than one computer, server computer, or some combination of computers and server computers, for example, a plurality of computers 102 communicating across the network 110 with a single server computer 114. In another embodiment, for example, the program 116 may operate on a plurality of server computers 114 communicating across the network 110 with a plurality of client computers. Alternatively, the program may operate on a network server communicating across the network with a server and a plurality of client computers.

The network 110 may include wired connections, wireless connections, fiber optic connections, or some combination thereof. In general, the network 110 can be any combination of connections and protocols that will support communications between the computer 102 and the server computer 114. The network 110 may include various types of networks, such as, for example, a local area network (LAN), a wide area network (WAN) such as the Internet, a telecommunication network such as the Public Switched Telephone Network (PSTN), a wireless network, a public switched network, a satellite network, a cellular network (e.g., a fifth generation (5G) network, a long-term evolution (LTE) network, a third generation (3G) network, a code division multiple access (CDMA) network, etc.), a public land mobile network (PLMN), a metropolitan area network (MAN), a private network, an ad hoc network, an intranet, a fiber optic-based network, or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of system 100 may perform one or more functions described as being performed by another set of devices of system 100.

Figure 2:
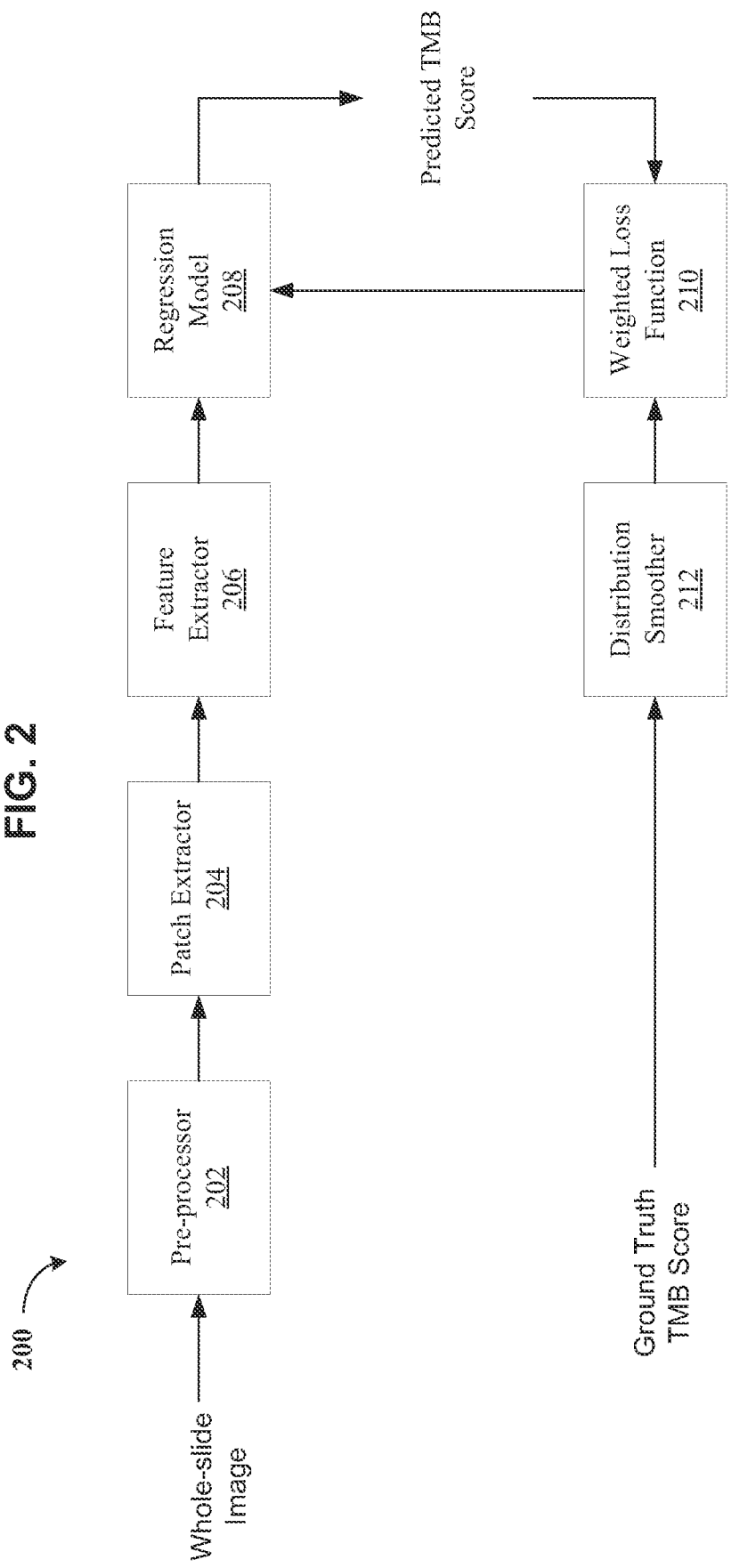
FIG. 2 is a block diagram of a deep learning system for image processing and genomic biomarker prediction, according to an embodiment.

FIG. 2 is a block diagram of genomic biomarker prediction method 200 to predict TMB scores based on histopathology images. Genomic biomarker prediction method 200 may include a pre-processor 202, a patch extractor 204, a feature extractor 206, a regression model 208, a weighted loss function 210, and a distribution smoother 212.

Embodiments of the present disclosure may be explained using specific datasets, specific techniques, to detect TMB scores associated with specific cancers. These exemplary embodiments are merely used as an example and are not intended to be limiting.

According to an aspect of the present disclosure, TMB scores computed from whole-exome sequencing (WES) of a dataset of carcinoma histopathology images may be used a ground truth. As an example, a publicly available dataset from the Cancer Genome Atlas (TCGA) for head and neck squamous cell carcinoma (HNSC) may be used. Other available datasets may be used as required and known in the art. Primary tumor samples for which both whole-slide image (WSI) and WES data are available may be selected from the dataset and used to determine ground truth. As an example, method 400 may used Hematoxylin and Eosin whole-slide images (H&E WSI) for which WES data is available. The pre-processor 202 may select only tissue regions in the process and remove background regions using traditional methods such as Otsu Thresholding or any other suitable technique, or advanced neural network-based methods. In some embodiments, the patch extractor 204 may extract patches of a predetermined size. As an example, the patch extractor 204 may extract patches of size 224×224 (112×112 microns) from each selected and/or pre-processed region and sample 8000 patches per image for feature extraction and regression. In some embodiments, the patch extractor 204 may not be used and whole medical images may be used. As an example, when devices with sufficient computing and memory are used, whole medical images may be used without extracting patches.

According to embodiments, subsequent to generating patches using the patch extractor, a neural network based (e.g., CNN-based, DNN-based) feature extractor 206 may extract features from the patches and a regression model 208 of one or more regression models may predict TMB score from the extracted features. The regression model 208 may predict the TMB score for each patch and the predictions of all patches may be averaged to obtain whole-slide image level (WSI) TMB score. In some embodiments, the regression model 208 may predict the TMB score for each patch and a highest predicted TMB score may be used to obtain whole-slide image level (WSI) TMB score. In some embodiments, the regression model 208 may predict the TMB score for each patch and the predictions of a highest predetermined number of patches may be averaged to obtain whole-slide image level (WSI) TMB score.

The TMB score may be determined using one or more pre-trained models or an end-to-end model. If one or more pre-trained models are used, a pre-trained neural network may be used for feature extraction and a trained an n-layer multilayer perceptron model may be used for TMB score determination. As an example, a pre-trained ResNet50 neural network may be used for feature extraction and a trained two-layer multilayer perceptron may be used for TMB determination. If an end-to-end model is used, both feature extractor 206 and regression model 208 may be trained simultaneously. An end-to-end model may also be used because it may have higher performance with fewer parameters as compared to other models, and hence may be easier to train on small datasets.

Distribution smoother 212 may be used to reduce the effect of imbalance in the continuous TMB score prediction. Label distribution smoothing (LDS) may be used to estimate a smoothed density of the TMB score labels. In the LDS method, a kernel density estimation may be used to convolve a symmetric kernel with TMB label density to generate a kernel-smoothed distribution of the TMB labels. The convolution operation takes into account the similarity in information of data samples at the nearby labels resulting in a smoothed label distribution which is less sparse compared to the original label distribution, and compensates for the missing TMB labels. As an example, Gaussian and Laplacian kernels may be used. In some embodiments, feature distribution smoothing (FDS) may be used estimate a smoothed feature space based on the features learnt by the feature extractor 206. In some embodiments, a combination of LDS and FDS may be used.

Based on the estimated smoothed distribution, weights may be computed for each TMB label by taking an inverse or square-root-inverse of the LDS estimated smoothed label density. This ensures that TMB labels which have smaller number of samples are given higher weightage during model training compared to TMB labels with larger number of samples, enabling the model to generalize well over the entire target range. These weights may be multiplied with a regression loss function, including but not limited to, mean-squared error (MSE), root mean squared error, Huber loss, mean absolute loss, for training the feature extraction and regression models using the following equation:

$$MSE = \frac{1}{N}\sum_{i=1}^{N} w^i * (y_{true}^i - y_{pred}^i)^2 \qquad \text{Eq. (1)}$$

Where i denotes the $i^{th}$ image out of total N training images, $w^i$ denotes the weight of the $i^{th}$ image, $y_{true}^i$ denotes the ground-truth and $y_{pred}^i$ denotes the predicted TMB score for the $i^{th}$ training image.

According to an aspect of the present disclosure, a predetermined number of samples may be selected from the dataset and be split into training, validation, and non-overlapping patients. The sampling may depend on the dataset used. The training set may be used to train the deep learning regression model, the validation set may be used for hyperparameter tuning and the test set may be used for evaluating performance against a baseline.

Figure 3:
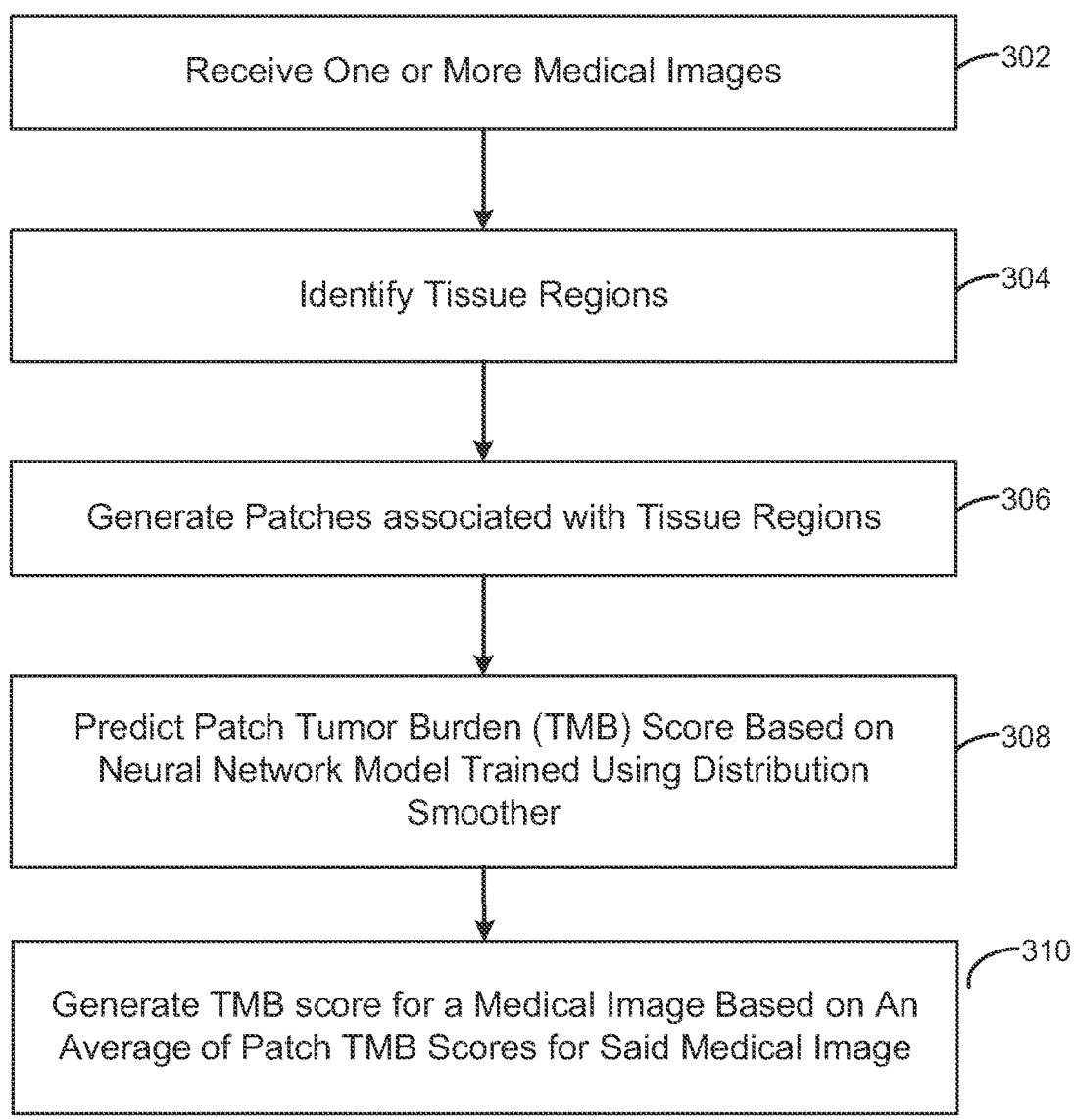
FIG. 3 is an exemplary flowchart illustrating image processing and genomic biomarker prediction, according to an embodiment.

FIG. 3 is a diagram illustrating an exemplary process 300 for image processing of histopathology images to predict a genomic biomarker using a neural network based method.

At operation 302, one or more medical images may be received. In some embodiments, one or more histopathology images may be received.

At operation 304, tissue regions in each of the one or more medical images may be identified. In some embodiments, tissue regions in each of the one or more histopathology images may be identified. As an example, the pre-processor 202 may identify tissue regions in each of the one or more histopathology images.

At operation 306, patches associated with respective identified tissue regions may be generated. As an example, the patch extractor 204 may be generated, the patches may be associated with respective identified tissue regions.

At operation 308, a patch tumor burden score for each of the patches may be predicted based on a neural network model, wherein the neural network model is trained using a distribution smoother and a weighted loss function. In some embodiments, the training the neural network model using the distribution smoother may include estimating a smooth density of a tumor burden score label based on similarity in information of data samples at nearby labels; computing weights for each tumor burden score label based on the smooth density of the tumor burden score label; and generating model weights for each tumor burden score label based on a loss function and the computed weights. As an example, the regression model 208 may predict a patch tumor burden score for each of the patches. As an example, the distribution smoother 212 and weighted loss function 210 may be used to train the regression model 208. The training may include using ground truth TMB score. In some embodiments, the neural-network based feature extractor and the neural network model may be trained simultaneously. The neural network model may be a regression model.

In some embodiments, the computed weights for each tumor burden score label based on the smooth density of the tumor burden score label may be inversely proportional to a number of samples belonging to respective tumor burden score label.

In some embodiments, prior to predicting the tumor burden score for each of the patches, operation 308 may include generating feature vectors based on the patches associated with the respective identified tissue regions using a neural-network based feature extractor, and wherein the feature vectors are used as input to the neural network model.

At operation 310, a tumor burden score for each of the one or more histopathology images may be generated based on an average of patch tumor burden score for patches associated with the respective identified tissue regions in respective histopathology images from the one or more histopathology images. In some embodiments, the patch tumor burden score may be classified based on predetermined thresholds.

Figure 4:
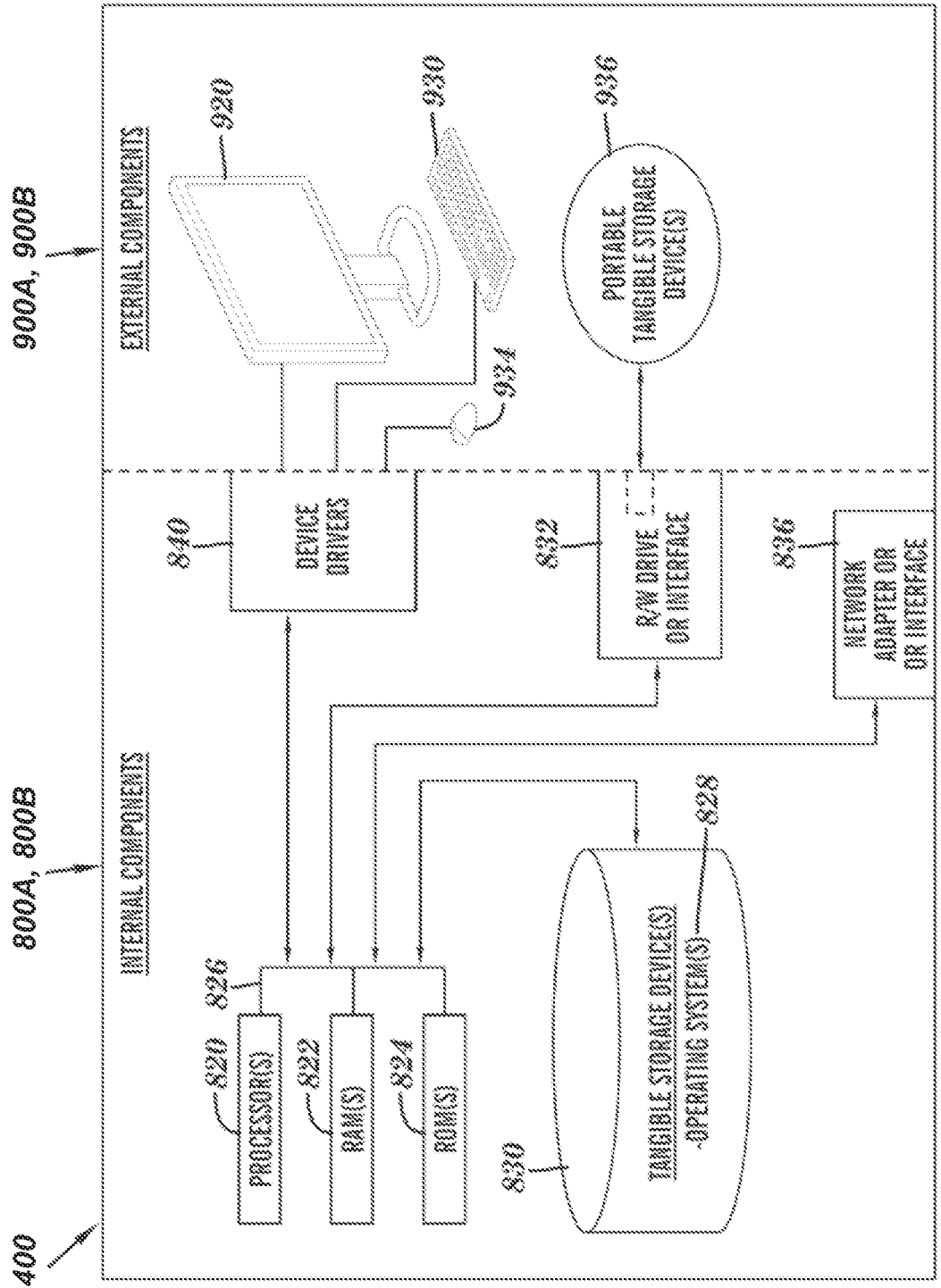
FIG. 4 is a block diagram of internal and external components of computers and servers depicted in FIG. 1 according to an embodiment.

FIG. 4 is a block diagram 400 of internal and external components of computers depicted in FIG. 1 in accordance with an illustrative embodiment. It should be appreciated that FIG. 4 provides only an illustration of one implementation and does not imply any limitations with regard to the environments in which different embodiments may be implemented. Many modifications to the depicted environments may be made based on design and implementation requirements.

Computer 102 (FIG. 1) and server computer 114 (FIG. 1) may include respective sets of internal components 800A,B and external components 900A,B. Each of the sets of internal components 800 include one or more processors 820, one or more computer-readable RAMs 822 and one or more computer-readable ROMs 824 on one or more buses 826, one or more operating systems 828, and one or more computer-readable tangible storage devices 830.

Processor 820 is implemented in hardware, firmware, or a combination of hardware and software. Processor 820 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 820 includes one or more processors capable of being programmed to perform a function. Bus 826 includes a component that permits communication among the internal components 800A,B.

The one or more operating systems 828, the software program 108 (FIG. 1) and the Genomic Biomarker Prediction Program 116 (FIG. 1) on server computer 114 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory, an optical disk, a magneto-optic disk, a solid state disk, a compact disc (CD), a digital versatile disc (DVD), a floppy disk, a cartridge, a magnetic tape, and/or another type of non-transitory computer-readable tangible storage device that can store a computer program and digital information.

Each set of internal components 800A,B also includes a R/W drive or interface 832 to read from and write to one or more portable computer-readable tangible storage devices 936 such as a CD-ROM, DVD, memory stick, magnetic tape, magnetic disk, optical disk or semiconductor storage device. A software program, such as the software program 108 (FIG. 1) and the Genomic Biomarker Prediction Program 116 (FIG. 1) can be stored on one or more of the respective portable computer-readable tangible storage devices 936, read via the respective R/W drive or interface 832 and loaded into the respective hard drive 830.

Each set of internal components 800A,B also includes network adapters or interfaces 836 such as a TCP/IP adapter cards; wireless Wi-Fi interface cards; or 3G, 4G, or 5G wireless interface cards or other wired or wireless communication links. The software program 108 (FIG. 1) and the Genomic Biomarker Prediction Program 116 (FIG. 1) on the server computer 114 (FIG. 1) can be downloaded to the computer 102 (FIG. 1) and server computer 114 from an external computer via a network (for example, the Internet, a local area network or other, wide area network) and respective network adapters or interfaces 836. From the network adapters or interfaces 836, the software program 108 and the Genomic Biomarker Prediction Program 116 on the server computer 114 are loaded into the respective hard drive 830. The network may comprise copper wires, optical fibers, wireless transmission, routers, firewalls, switches, gateway computers and/or edge servers.

Each of the sets of external components 900A,B can include a computer display monitor 920, a keyboard 930, and a computer mouse 934. External components 900A,B can also include touch screens, virtual keyboards, touch pads, pointing devices, and other human interface devices. Each of the sets of internal components 800A,B also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Some embodiments may relate to a system, a method, and/or a computer readable medium at any possible technical detail level of integration. The computer readable medium may include a computer-readable non-transitory storage medium (or media) having computer readable program instructions thereon for causing a processor to carry out operations.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program code/instructions for carrying out operations may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects or operations.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer readable media according to various embodiments. In this regard, each block in the flowchart or block diagrams may represent a module, segment, or portion of instructions, which comprises one or more executable instructions for implementing the specified logical function(s). The method, computer system, and computer readable medium may include additional blocks, fewer blocks, different blocks, or differently arranged blocks than those depicted in the Figures. In some alternative implementations, the functions noted in the blocks may occur out of the order noted in the Figures. For example, two blocks shown in succession may, in fact, be executed concurrently or substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The descriptions of the various aspects and embodiments have been presented for purposes of illustration, but are not intended to be exhaustive or limited to the embodiments disclosed. Even though combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A neural network based method for image processing of medical images, executable by one or more processors, the method comprising:
   receiving one or more medical images;
   identifying tissue regions in each of the one or more medical images;
   generating patches associated with respective identified tissue regions;
   predicting a patch tumor burden score for each of the patches based on a neural network model, wherein the neural network model is trained using a distribution smoother and a weighted loss function, wherein TMB labels are smoothed with a Gaussian or Laplacian kernel, and wherein features in a feature space are smoothed using feature distribution smoothing and wherein weights are computed for each TMB label by using an inverse of the LDS estimated smoothed label density;
   generating a tumor burden score for each of the one or more medical images based on the patch tumor burden score for patches associated with the respective identified tissue regions in respective medical images from the one or more medical images, wherein the tumor burden score of the one or more medical images is drawn from a continuous TMB score range;
   providing, based on the continuous TMB score range, flexibility to a pathologist to select a threshold; and
   separating, based on at least on tumor burden score of the one or more medical images and using the threshold set by the pathologist, a patient into a first set of responding patients or into a second set of non-responding patients based on the threshold.

2. The method of claim 1, wherein training the neural network model using the distribution smoother comprises: estimating a smooth density of a tumor burden score label based on similarity in information of data samples at nearby labels;
   computing weights for each tumor burden score label based on the smooth density of the tumor burden score label; and
   generating model weights for the each tumor burden score label based on a loss function and the computed weights.

3. The method of claim 2, wherein the computed weights for the each tumor burden score label based on the smooth density of the tumor burden score label are inversely proportional to a number of samples belonging to respective tumor burden score label.

4. The method of claim 1, wherein prior to predicting the tumor burden score for each of the patches, the method comprises generating feature vectors based on the patches associated with the respective identified tissue regions using a neural-network based feature extractor, and wherein the feature vectors are used as input to the neural network model.

5. The method of claim 4, wherein the neural-network based feature extractor and the neural network model are trained simultaneously.

6. The method of claim 1, wherein the method further comprises classifying the patch tumor burden score based on predetermined thresholds.

7. The method of claim 1, wherein the generating the tumor burden score is based on an average of the patch tumor burden score for a predetermined number of patches associated with the respective identified tissue regions in respective medical images from the one or more medical images.

8. An apparatus for a neural network based framework for image processing of medical images, the apparatus comprising:
   a memory storing instructions; and
   at least one processor configured to execute the instructions to:
      receive one or more medical images;
      identify tissue regions in each of the one or more medical images;
      generate patches associated with respective identified tissue regions;
      predict a patch tumor burden score for each of the patches based on a neural network model, wherein the neural network model is trained using a distribution smoother and a weighted loss function, wherein TMB labels are smoothed with a Gaussian or Laplacian kernel, and wherein features in a feature space are smoothed using feature distribution smoothing and wherein weights are computed for each TMB label by using an inverse of the LDS estimated smoothed label density;
   generate a tumor burden score for each of the one or more medical images based on the patch tumor burden score for patches associated with the respective identified tissue regions in respective medical images from the one or more medical images, wherein the tumor burden score of the one or more medical images is drawn from a continuous TMB score range;
   provide, based on the continuous TMB score range, flexibility to a pathologist to select a threshold; and
   separate, based on at least on tumor burden score of the one or more medical images and using the threshold set by the pathologist, a patient into a first set of responding patients or into a second set of non-responding patients based on the threshold.

9. The apparatus of claim 8, wherein the at least one processor is further configured to execute instructions to train the neural network based framework using the distribution smoother:
estimate a smooth density of a tumor burden score label based on similarity in information of data samples at nearby labels;
compute weights for each tumor burden score label based on the smooth density of the tumor burden score label; and
generate model weights for the each tumor burden score label based on a loss function and the computed weights.

10. The apparatus of claim 9, wherein the computed weights for the each tumor burden score label based on the smooth density of the tumor burden score label are inversely proportional to a number of samples belonging to respective tumor burden score label.

11. The apparatus of claim 8, wherein prior to predicting the tumor burden score for each of the patches, the at least one processor further configured to execute the instructions to generate feature vectors based on the patches associated with the respective identified tissue regions using a neural-network based feature extractor, and wherein the feature vectors are used as input to the neural network model.

12. The apparatus of claim 11, wherein the neural-network based feature extractor and the neural network model are trained simultaneously.

13. The apparatus of claim 8, wherein the patch tumor burden score is based on predetermined thresholds.

14. The apparatus of claim 8, wherein the generating the tumor burden score is based on an average of the patch tumor burden score for a predetermined number of patches associated with the respective identified tissue regions in respective medical images from the one or more medical images.

15. A non-transitory computer-readable medium storing instructions for a neural network based method for image processing of medical images, the instructions comprising:
one or more instructions that, when executed by one or more processors, cause the one or more processors to:
receive one or more medical images;
identify tissue regions in each of the one or more medical images;
generate patches associated with respective identified tissue regions;
predict a patch tumor burden score for each of the patches based on a neural network model, wherein the neural network model is trained using a distribution smoother and a weighted loss function, wherein TMB labels are smoothed with a Gaussian or Laplacian kernel, and wherein features in a feature space are smoothed using feature distribution smoothing and wherein weights are computed for each TMB label by using an inverse of the LDS estimated smoothed label density;
generate a tumor burden score for each of the one or more medical images based on the patch tumor burden score for patches associated with the respective identified tissue regions in respective medical images from the one or more medical images, wherein the tumor burden score of the one or more medical images is drawn from a continuous TMB score range;
provide, based on the continuous TMB score range, flexibility to a pathologist to select a threshold; and
separate, based on at least on tumor burden score of the one or more medical images and using the threshold set by the pathologist, a patient into a first set of responding patients or into a second set of non-responding patients based on the threshold.

16. The non-transitory computer-readable recording medium according to claim 15, further comprising instructions to train the neural network based framework using the distribution smoother, the instructions to train that, when executed by the one or more processors, cause the one or more processors to:
estimate a smooth density of a tumor burden score label based on similarity in information of data samples at nearby labels;
compute weights for each tumor burden score label based on the smooth density of the tumor burden score label; and
generate model weights for the each tumor burden score label based on a loss function and the computed weights.

17. The non-transitory computer-readable recording medium according to claim 16, wherein the computed weights for the each tumor burden score label based on the smooth density of the tumor burden score label are inversely proportional to a number of samples belonging to respective tumor burden score label.

18. The non-transitory computer-readable recording medium according to claim 15, wherein prior to predicting the tumor burden score for each of the patches, the one or more instructions that, when executed by the one or more processors, cause the one or more processors to generate feature vectors based on the patches associated with the respective identified tissue regions using a neural-network based feature extractor, and wherein the feature vectors are used as input to the neural network model.

19. The non-transitory computer-readable recording medium according to claim 18, wherein the neural-network based feature extractor and the neural network model are trained simultaneously.

20. The non-transitory computer-readable recording medium according to claim 15, wherein the patch tumor burden score is based on predetermined thresholds.

* * * * *